United States Patent [19]
Singh et al.

[11] Patent Number: 5,874,402
[45] Date of Patent: Feb. 23, 1999

[54] USE OF CELL MEMBRANE PERMEANTS IN THE TREATMENT OF CELLULAR PROLIFERATIVE DISEASES

[75] Inventors: Saira Singh, Los Gatos; Richard E. Jones, Palo Alto; Dennis M. Brown, San Mateo, all of Calif.

[73] Assignee: Matrix Pharmaceutical, Inc., Fremont, Calif.

[21] Appl. No.: 857,736

[22] Filed: May 16, 1997

Related U.S. Application Data

[62] Division of Ser. No. 604,312, Feb. 21, 1996, abandoned.

[51] Int. Cl.$^6$ .......................... A61K 38/00; A61K 31/435

[52] U.S. Cl. .......................... 514/2; 424/195.11; 424/450; 424/484; 424/485; 424/458; 514/3; 514/183; 514/283; 514/781; 514/782; 514/801; 514/802; 514/946; 514/947

[58] Field of Search ...................... 424/450, 484, 424/485, 488, 195.11; 514/2, 772, 777, 781, 782, 801, 802, 3, 183, 283, 946, 947

[56] References Cited

U.S. PATENT DOCUMENTS

| Re. 33,375 | 10/1990 | Luck et al. | 514/2 |
|---|---|---|---|
| 5,273,965 | 12/1993 | Kensil et al. | 514/3 |

OTHER PUBLICATIONS

Jekunen et al., "Modulation of Cisplatin Cytotoxicity by Permeabilization of the Plasma Membrane by Digitonin in vitro," *Biochemical Pharmacology*, 45:2079–2085 (1993).

*Primary Examiner*—Richard L. Raymond
*Attorney, Agent, or Firm*—Flehr Hohbach Test Albritton & Herbert LLP

[57] ABSTRACT

Methods are provided for the treatment of a host suffering from a cellular proliferative disease through administration of a chemotherapeutic agent in conjunction with a cell membrane permeant. Optionally, the cell membrane permeant and/or chemotherapeutic agent will be present in a pharmaceutically acceptable vehicle capable of acting as a depot. In the subject methods, the chemotherapeutic agent and membrane permeant are administered at least proximal to a target site of the host. Administration of chemotherapeutic agents in accordance with the subject methods results in improved efficacy of, and/or decreased host toxicity to, the intralesionally administered chemotherapeutic agent.

29 Claims, No Drawings

USE OF CELL MEMBRANE PERMEANTS IN THE TREATMENT OF CELLULAR PROLIFERATIVE DISEASES

This is a divisional of application Ser. No. 08/604,312 filed Feb. 21, 1996, now abandoned.

FIELD OF THE INVENTION

The field of this invention is the chemotherapeutic treatment of cellular proliferative diseases.

BACKGROUND

Of increasing interest in the treatment of cellular proliferative or neoplastic diseases is the use of chemotherapeutic agents, either alone or in combination with other treatments, such as surgical, radio- or immunotherapeutic procedures. Since the majority of chemotherapeutic agents tend to exert their antiproliferative activity on a host's cells in a non-specific manner, the dosage that may be administered during a particular treatment is often limited by the systemic toxicity of the agent, i.e. the host's toxic reaction to the presence of the agent.

In order to avoid dose limiting systemic toxicity, methods of local and regional administration of chemotherapeutic agents may be employed, particularly with cellular proliferative diseases characterized by the presence of solid tumors or neoplasms. In local administration, the chemotherapeutic agent is administered at the site of the neoplasm, i.e. intralesionally, while in regional administration the drug is directed to the target organ or tissue after intraarterial, intravesicular, intraperitoneal or subconjunctival administration. The goal of local and regional administration is to limit the systemic exposure of the host to the agent and yet maintain a relatively high concentration of the agent at the site or in the region of administration, thereby providing the possibility of improved antiproliferative activity with reduced host toxicity. However, despite the promise of local and regional administration, with some chemotherapeutic agents successful results have not yet been realized. Problems which have been encountered with some agents are rapid diffusion from the site of administration and/or insufficient internalization of the agent by the abnormal quiescent and proliferative cells. Insufficient internalization of the agent is problematic where high, and potentially systemically toxic, dosages of agent must be administered to achieve a sufficiently high intracellular concentration of the agent.

Accordingly, there is continued interest in the development of improved methods of local and regional administration. Improved methods would provide for increased efficacy and/or reduced systemic toxicity of the local or regionally administered agent.

Relevant Literature

U.S. Pat. No. RE 33,375 reports the use of proteinaceous matrix delivery vehicles for the intralesional administration of cellular antiproliferative agents. U.S. Pat. No. 5,273,965 reports the preparation and use of modified saponins to enhance the transport of pharmaceutically active agents across mucous membranes. Jekunen et al., Biochem. Pharmacol. (1993) 45: 2079–2085 reports on the enhanced uptake of cisplatin by ovarian cancer cells ice vitro when the cells are first exposed to digitonin.

Debs et al., "*Immunomodulatory and Toxic Effects of Free and Liposome-Encapsulated Tumor Necrosis Factor α in Rats*," Cancer Res. (1990) 50: 375, reports the administration of Tumor Necrosis Factor (TNF) encapsulated in liposomes.

A review of drugs used for the treatment of cellular proliferative diseases is provided in Pratt et al., The Anti-cancer Drugs (1994).

SUMMARY OF THE INVENTION

Methods are provided for the treatment of host suffering from a cellular proliferative disease through the administration of a chemotherapeutic agent in conjunction with a cell membrane permeant. The cell membrane permeant and/or chemotherapeutic agent may optionally be administered in a pharmaceutically acceptable vehicle capable of acting as a depot, either short or long term. In the subject methods, the chemotherapeutic agent and membrane permeant are administered at least proximal to a target site of the host. With the subject methods, relatively greater anti-cellular proliferative activity and/or reduced systemic toxicity of the intralesionally administered chemotherapeutic agent is achieved. The subject methods find particular application in the intralesional delivery of chemotherapeutic agents that act intracellularly.

DESCRIPTION OF THE SPECIFIC EMBODIMENTS

Methods are provided for the treatment of a host suffering from a cellular proliferative disease through administration of a chemotherapeutic agent in conjunction with a cell membrane permeant. The cell membrane permeant and/or chemotherapeutic agent are optionally administered in a pharmaceutically acceptable vehicle capable of acting as a depot. In the subject methods, the agent and permeant are administered at least proximal to a target site of the host. By administering chemotherapeutic agents in accordance with the subject methods, relatively greater efficacy and/or reduced systemic toxicity are achieved.

Critical to the subject methods is the use of a cell membrane permeant. In the subject methods, at least one cell membrane permeant will be administered, where in some instances a combination of two or more, generally not more than four, different membrane permeants may be administered. Cell membrane permeants that may be employed in the subject invention are those agents which are pharmaceutically acceptable at the administered dosage levels and serve to modulate the permeability properties of abnormally proliferative, abnormally quiescent, malignant or diseased cell membranes with respect to the chemotherapeutic agent being administered. In modulating the properties of the cell membrane with respect to the chemotherapeutic agent, the membrane permeant may serve to increase the influx into the cell, and/or decrease the efflux from the cell, of the chemotherapeutic agent, thereby increasing the achievable intracellular concentration of the chemotherapeutic agent. Generally, the cell membrane permeant will be an agent that is capable of disrupting the integrity of the membrane so that the membrane is structurally frailed, i.e. the membrane becomes perforated and leaky. The agent may disrupt the integrity of the membrane in a number of different ways. For example, the agent may incorporate into the membrane to disrupt the orderly packing of the lipid constituents of the membrane. Alternatively, the agent may interact with a membrane constituent, e.g. a steroid, to disrupt the integrity of the membrane. Agents capable of disrupting the integrity of the cell membrane include: lysoplasmologens, e.g. lysolecithins; surfactants, e.g. polyoxyethylated sorbitans, polysorbates, sorbitan esters etc.; detergents, e.g. sodium dodecylsulfate (SDS); and the like. Other cell membrane permeants capable of disrupting the integrity of the membrane include membrane permeants that comprise an extended ring structure which provides for the disruption of the orderly packing of the lipid cell membrane molecules. Cell membrane permeants having extended ring structures include steroidal and triterpenoid glycosides such as: saponins, e.g. saponaria officinalis and quillaira saponaria; bile acids, e.g. cholic acid and taurocholic acid; constituents of digitalis, e.g. digitalin, digitonin and digitoxin, as well as derivatives thereof, such as digitogenin, digitoxigenin, digoxigenin, and digoxin; fusidic acid and derivatives thereof, and the like. Cell membrane permeants which disrupt the integrity of the membrane through interaction with membrane constituents, e.g. by binding to membrane components such as steroid, phospholipids and the like, include amphotericin B, melittin, polymyxin B, and the like.

The cell membrane permeant may be administered in a variety of different vehicles. Depending on the particular vehicle employed, the composition comprising the membrane permeant which is administered may be formulated as a solution, suspension, dispersion, emulsion and the like, as long as the formulation is injectable.

By injectable is meant that the formulation will be flowable, at least at some point, so that it can be introduced via a syringe or catheter. The flowable membrane permeant formulation will generally have a viscosity ranging from 1 to 50,000 mPa·sec, usually from about 1 to 40,000 mPa·sec.

A number of different vehicles are suitable for delivery of the membrane permeant, with the particular vehicle being chosen based on the particular permeant and chemotherapeutic agent to be administered. The vehicles will be pharmaceutically acceptable when administered and may be aqueous or substantially anhydrous, where the substantially anhydrous vehicles employed may be water miscible or immiscible. Suitable pharmaceutically acceptable aqueous or predominantly aqueous vehicles include ionic solutions, deionized water, oil-in-water emulsions, liposomes and the like.

Instead of aqueous vehicles, the membrane permeant may be administered in a non-aqueous or predominantly non-aqueous vehicle, such as alkanols, e.g. ethanol, propylene glycol, semi-solid glyceride mixtures, water-in-oil emulsions, and the like.

In some instances, in order to obtain greater efficacy and/or further reduce host systemic toxicity to the presence of the agent, the cell membrane permeant and/or chemotherapeutic agent may be administered in a vehicle capable of acting as a depot, i.e. at least one of the membrane permeant and chemotherapeutic agent will be administered in a depot vehicle. In vehicles capable of acting as a depot, the vehicle will limit the systemic dispersion of the membrane permeant from the site of injection and thereby maintain the cell membrane permeant in the region of administration. Since the active agent will be administered in conjunction with the membrane permeant, when the membrane permeant is delivered in a vehicle capable of acting as a depot, the vehicle will generally act as a depot for the active agent as well, whether the active agent is introduced after introduction of the membrane permeant or at the same time as the membrane permeant. Of interest as vehicle depots are the lipophilic compositions described in PCT/US94/14559, the disclosure of which is herein incorporated by reference. Liposomes may also find use as depot delivery vehicles. Other vehicle depots that may be employed as carrier vehicles for membrane permeants include compositions comprising one or more thickening agents including carbohydrates, such as agarose and dextrans; cellulose; gums; and other thickening agents, where the compositions may be aqueous, partially aqueous or nonaqueous. Also suitable for use as vehicle depots are those vehicles which, following injection, are capable of setting up into a solid or viscous semisolid mass. Such vehicles include silicones, calcium phosphates, polylactic acid polymers and the like. Of particular interest are the proteinaceous depot compositions described in U.S. Pat. No. RE 33,375, the disclosure of which is herein incorporated by reference, e.g. fibrinogen, albumin, and especially collagen.

The amount of membrane permeant in the administered composition will depend on a variety of factors, including the nature of the permeant, the nature of the vehicle employed, the nature of the drug and the like. Generally, the membrane permeant will be present in the vehicle in the range from about 0.1 to 80 weight %, usually from about 1.0 to 50 weight %. The amount of membrane permeant present in the composition will be sufficient to deliver a permeant dosage to the host generally ranging from 0.001 to 50 mg/kg host, more generally from about 0.01 to 40 mg/kg of host.

With a variety of chemotherapeutic agents, increased efficacy and/or reduced systemic toxicity will be achieved by employing the subject methods. Chemotherapeutic agents employed in the subject methods will be those agents that exhibit anticellular proliferative activity on the abnormally proliferative cells. In other words, the abnormally proliferative cells of the cellular proliferative disease will be susceptible to treatment with the chemotherapeutic agent employed. In exhibiting antiproliferative activity, the agent may have a cytostatic or cytotoxic effect on the abnormally proliferative cells. A large number of chemotherapeutic agents are known in the art, including those reviewed in Pratt et al., The Anticancer Drugs (1994).

Of interest is the use of the subject methods to deliver chemotherapeutic agents that exhibit their activity intracellularly to at least slow the rate of cellular proliferation. A variety of agents exhibit anti-cellular proliferative activity through interference or modulation of intracellular mechanisms associated with cellular proliferation, e.g. DNA transcription or translation, signal transduction, cell division, and the like. Intracellular acting agents include: peptide, polypeptide and protein therapeutics; nucleic acids and oligonucleotides; naturally occurring and synthetic organic compounds, as well as mimetics thereof.

Polypeptide and protein therapeutic agents which may be administered by the subject methods will be at least about 5 kDa, and will usually be at least about 10 kDa, more usually at least about 12 kDa, and will generally not exceed a molecular weight of about 200 kDa, and will usually not exceed 150 kDa. Protein therapeutic agents include cytokines such as interferons, e.g. interferon-$\alpha$, and naturally occurring cytotoxic factors, such as TNF-$\alpha$ (tumor necrosis factor-$\alpha$) and TNF-$\beta$ (tumor necrosis factor-$\beta$ or lymphotoxin), monoclonal and polyclonal antibodies, and the like. Also of interest is the delivery of nucleic acids and oligonucleotides, such as DNA comprising a gene capable of modulating the proliferation of the cell or anti-sense RNA. See Pratt, szipra, pp. 297–299. Also of interest are chromatin function inhibiting agents, including: microtubule inhibitors such as taxoids, e.g. paclitaxel and synthetic derivatives thereof and vinca alkaloids and derivatives thereof, e.g. vinblastine, vincristine, vindesine, navelbine; topoisomerase inhibitors such as camptothecin and derivatives thereof, e.g. CPT-11, and the like. Other compounds which interfere with signal transduction mechanisms and thereby reduce cellular proliferation include tyrosine kinase inhibitors, such as Tyr 47 and AG 126, neomycin sulfate, and the like.

The chemotherapeutic agents may be administered in a pharmaceutically acceptable vehicle distinct from the vehicle used to introduce the cell membrane permeant, or may be combined with the membrane permeant in the same vehicle. Where the chemotherapeutic agent is administered in a vehicle distinct from the membrane permeant, any of the above vehicles used for the delivery of the membrane permeant that are convenient may be employed. Whether administered in a separate vehicle or the same vehicle as the permeant, the concentration of the chemotherapeutic agent in the vehicle will depend on a number of factors, such as the particular agent employed, the systemic toxicity of the agent, whether the agent is to be administered once or a number of times, the nature of the membrane permeant and vehicle, and the like, with the optimal dosage being determined empirically. Generally, the amount of chemotherapeutic agent in the administered composition will range from 0.1 to 50% by weight, usually 1.0 to 50% weight. The amount of agent that is introduced will be sufficient to provide a single dosage to the host ranging from 0.01 to 100 mg/kg host, usually from about 0.02 to 20 mg/kg host.

The compositions which are administered in the subject methods may further comprise a number of minor components which serve a variety of purposes. These minor components will, for the most part, impart properties which protect the stability of the composition, control the pH, or the like. Various excipients may also be employed, as is known the art. These minor excipients will generally be present in less than about 10 weight percent of the total composition, usually less than about 2 weight percent, and individually may vary from about 0.001 weight percent to about 1 weight percent of the total composition.

As mentioned above, critical to the subject methods is the administration of the membrane permeant in conjunction with the active, chemotherapeutic agent. By "in conjunction with" is meant that the cell membrane permeant is administered anywhere from simultaneously to up to 5 hours prior to the chemotherapeutic agent. Thus, the cell membrane permeant and chemotherapeutic agent may be administered either: (a) sequentially, with the cell membrane permeant being administered prior to the chemotherapeutic agent or (b) simultaneously. Where the cell membrane permeant is administered prior to the chemotherapeutic agent, it will usually be administered between 0.5 and 5.0 hours prior to administration of the therapeutic agent, usually between about 1.0 and 3.0 hours prior to administration of the therapeutic agent. Where the cell membrane permeant is administered simultaneously with the chemotherapeutic agent, the two components may be administered as either a single, combined composition or as two distinct compositions that are simultaneously administered at substantially the same site of the neoplastic lesion. Whether the membrane permeant and active agent are administered simultaneously as a single combination composition or as two distinct compositions will depend on the particular agent employed, as well as the membrane permeant and vehicle used. Thus, with some chemotherapeutic agents, better efficacy and or reduced systemic toxicity are achieved through administration of a single composition comprising the permeant, active agent and, if present, the depot vehicle. With other chemotherapeutic agents, the best results will be obtained by administering the permeant and chemotherapeutic agent as separate compositions. Which is preferred may be readily determined empirically using the model provided in the experimental section.

In the subject methods, the chemotherapeutic agent and membrane permeant will be administered at least proximal to at least one target site of the host, where target site is defined as a location of a lesion of the cellular proliferative disease afflicting the host or patient, e.g. neoplasm. Thus, in the subject methods the agent and permeant may be administered either regionally or locally. For regional administration, the agent and permeant may be administered intraarterially, intravesicularly, intraperitoneally, subconjunctivally and the like. With regional administration, the agent and permeant are directed to a particular target organ or tissue, resulting in an increased concentration of the agent and permeant at the target site as compared with their systemic concentration. Where the agent and permeant are administered locally, they will be administered directly at the site of a lesion of cellular proliferative disease, i.e. intralesionally or intratumorally.

Depending on the cellular proliferative disease to be treated, over the entire course of treatment, it may be sufficient to administer the membrane permeant and chemotherapeutic agent only once. The individual treatment may include a single injection or a plurality of injections at different sites depending on the nature and size of the lesion. In other instances, a plurality of administrations at different times may be employed, where the cell membrane permeant and chemotherapeutic agent are introduced at the site of the lesion more than one time. Generally, when a plurality of administrations is employed, the cell membrane permeant/chemotherapeutic agent will be administered at least two times, usually at least three times, and usually not more than eight times, more usually not more than six times. The decision to employ a plurality of administrations will depend upon the lifetime of the drug at the tumor site and the response of the tumor to the drug, as well as the observed toxicity of the drug to the host. The use of a plurality of administrations may provide for the possibility of using a lower dosage of chemotherapeutic agent per administration, thereby reducing the host toxicity in response to the presence of the agent without a concomitant loss in the overall anti-cellular activity of the chemotherapeutic agent. Where a plurality of administrations are employed, administration may be hourly, daily, weekly, or less frequently, e.g. every two weeks or monthly.

Any means of introducing the membrane permeant and chemotherapeutic agents at least proximal to a target site of the host, i.e. intralesionally, may be employed. Thus, syringes, catheters or other convenient means that allow for the introduction of a flowable composition at the site of the tumor may be used. The volume of the cell membrane permeant and/or chemotherapeutic agent composition that is intralesionally introduced will depend on the host size, tumor size and the like, and will generally range from 0.25 to 50 ml, usually from 0.5 to 30 ml, and more usually from 1.0 to 20 ml.

In the subject methods, over the course of an entire treatment, where the membrane permeant and chemotherapeutic agents may be administered only once or a plurality of the times, the amount of chemotherapeutic agent administered to the host at the tumor site will be effective to treat the host suffering from the cellular proliferative disease, i.e. be sufficient to at least slow the rate of proliferation, and will generally range from about 0.1 to 500, more usually about 0.3 to 300 mg/kg of host, depending upon the nature of the drug, the size of tumor, the systemic toxicity of the agent, the nature of the delivery vehicle employed, and the like. In view of the wide diversity of tumors, the varying nature of tumors, the effective concentration of drug, the relative mobility and the like, as well as the possibility for multiple administrations, a definitive range cannot be specified. With each drug and each tumor, experience will provide an optimum dosage level.

The subject methods find use in the treatment of a wide variety of hosts suffering from any one of a multitude of cellular proliferative diseases. Hosts that may be treated with the subject methods will be mammalian and include: rare or highly valuable animals, domestic animals, e.g. dogs and cats, and humans. Cellular proliferative diseases that may be treated with the subject methods will be those cellular proliferative diseases characterized by the presence of solid tumors or neoplasms, and include carcinomas, sarcomas and melanomas, such as basal cell carcinoma, squamous cell carcinoma, melanoma, soft tissue sarcoma, solar keratoses, Kaposi's sarcoma, cutaneous malignant lymphoma, Bowen's disease, Wilm's tumor, hepatomas, colorectal cancer, brain tumors, mycosis fungoides, Hodgkins lymphoma, polycythemia vera, lymphomas, oat cell sarcoma, superficial and invasive bladder tumors, ovarian cancer, etc.

By administration of chemotherapeutic agents according to the subject invention, treatment of hosts suffering from cellular proliferative disease can be achieved through at least a decrease in the rate of progression of the disease, e.g. a decrease in the rate of cellular proliferation. Thus, by administering chemotherapeutic agents in accordance with the subject methods, the rate of progression of the cellular proliferative disease will at least be slowed. In some instances administration of chemotherapeutic agents according to the subject methods will result in a complete cessation in the progression of the disease, as manifested by a cessation in abnormal cellular proliferation and function.

Conveniently, kits are provided that comprise the cell membrane permeant and intracellularly acting chemotherapeutic agent. The kits will further comprise, where desired, a pharmaceutically acceptable vehicle capable of acting as a depot, where at least one of the cell membrane permeant and chemotherapeutic agent are present in the vehicle. The kit may also comprise a means for injecting the membrane permeant and chemotherapeutic agent, where the means may be a syringe, catheter or other suitable administration means. In some instances, the cell membrane permeant and chemotherapeutic components of the kit may both be combined with a pharmaceutically acceptable vehicle to make a single composition capable of administration.

The following examples are offered by way of illustration and not by way of limitation.

EXPERIMENTAL

For each of the following experiments, transplantable murine fibrosarcoma RIF-1 tumors were grown intradermally in the flank of 3–7 month old female C3H mice ($2 \times 10^5$ cells were injected). When the introduced tumors reached 100 mm$^3$, the mice were ready for testing. During the course of the experiments, the treated and control tumors were measured three times per week by Vernier calipers and the tumor volumes were calculated using the following formula:

$$V = \pi/6 \times D_1 \times D_2 \times D_3$$

where $D_1$–$D_3$ are tumor diameters in millimeters. The number of days for tumors to reach four times (4×) their baseline volume was used as a parameter of treatment effectiveness. Therefore, a longer delay in tumor growth meant greater antitumor efficacy.

EXAMPLE 1
Administration of Saponin (a cell membrane permeant) in Conjunction with Tumor Necrosis Factor (TNF, a polypeptide antitumor cytokine)

TABLE 1

Influence of Saponin, With and Without Collagen Gel Delivery Matrix, on TNF Efficacy (0.1 and 0.3 mg/kg) in RIF-1 Murine Tumors: Single vs. Multiple Doses

| Grp | Treatment | # of Treatments | Dose (mg/kg) | # of Tumors | Days to 4× Tumor Volume Treated | Untreated |
|---|---|---|---|---|---|---|
| 1 | Untreated Control | — | — | 4 | — | 6.6 ± 0.4 |
| 2 | Siponin | 1 | 10 | 5 | 7.5 ± 0.6 | — |
| 3 | Saponin/CM | 1 | 10 | 5 | 7.8 ± 0.5 | — |
| 4 | TNF | 1 | 0.3 | 5 | 7.8 ± 0.5 | — |
| 5 | Sap(1h)->TNF[1] | 1 | 10, 0.3 | 4 | 11.2 ± 0.9 | — |
| 6 | Sap/CM(1h)->TNF[2] | 1 | 10, 0.3 | 5 | 15.4 ± 1.2 | — |
| 7 | TNF | 5 | 0.1 | 5 | 8.2 ± 0.3 | — |
| 8 | Sap(1h)->TNF[1] | 5 | 10, 0.1 | 5 | 16.0 ± 4.9 | — |
| 9 | Sap/CM(1h)->TNF[2] | 5 | 10, 0.1 | 5 | 15.8 ± 1.9 | — |

[1]Treatment with saponin one hour prior to TNF injection.
[2]Treatment with saponin and collagen gel delivery matrix (2% collagen) one hour prior to TNF injection.

The above results demonstrate that by intralesionally administering saponin prior to intralesional administration of TNF, the efficacy of the TNF is enhanced, as evidenced by the increase in time until 4× tumor volume is achieved. This enhancement by saponin is greater than the slight effects observed for saponin controls (groups 2 & 3).

TABLE 2

Enhancement of Efficacy and Reduction of Lethal Toxicity After Intratumoral Injection of TNF with Saponin in Collagen Gel Delivery Matrix in RIF-1 Tumors in C3H Mice

| Grp | Treatment | Dose (mg/kg) | # of Tumors | Days to 4x Tumor Volume Treated | Days to 4x Tumor Volume Untreated | # of Deaths/ # of mice |
|---|---|---|---|---|---|---|
| 1 | Untreated Control | — | 8 | — | 7.1 ± 0.14 | 0/4 |
| 2 | Saponin | 10 | 5 | 8.7 ± 0.53 | — | 0/5 |
| 3 | Saponin/CM | 10 | 4 | 6.6 ± 0.38 | — | 1/5 |
| 4 | TNF | 0.5 | 6 | 7.7 ± 0.30 | — | 0/6 |
| 5 | Sap(1h)->TNF[1] | 10, 0.5 | 1 | 15.6 | — | 5/6 |
| 7 | Sap/CM(1h)->TNF[2] | 10, 0.5 | 5 | 17.0 ± 1.33 | — | 1/6 |
| 8 | Sap/CM/TNF[3] | 10, 0.8 | 4 | 17.5 ± 1.5 | — | 2/6 |

[1]Treatment with saponin one hour prior to TNF injection.
[2]Treatment with saponin and collagen gel delivery matrix one hour prior to TNF injection.
[3]One syringe containing a mixture of saponin, collagen gel delivery matrix and TNF

TABLE 3

TNF Dose-Response: Summary of Experiments Demonstrating Reduced Toxicity of Intratumoral Injection of TNF and Saponin in Collagen Gel Delivery Matrix

| Grp | Treatment | Dose (mg/kg) | # of Mice Injected | # of Deaths | % Death |
|---|---|---|---|---|---|
| 1 | Untreated Control | — | 12 | 0 | 0 |
| 2 | Saponin | 10 | 16 | 1 | 6.3 |
| 3 | Saponin/CM | 10 | 17 | 1 | 5.9 |
| 4 | TNF | 0.3 | 12 | 0 | 0 |
| 5 | Sap(1h)->TNF[1] | 10, 0.3 | 12 | 7 | 58.3 |
| 6 | Sap/CM(1h)->TNF[2] | 10, 0.3 | 11 | 0 | 0 |
| 7 | TNF | 0.5 | 18 | 0 | 0 |
| 8 | Sap(1h)->TNF[1] | 10, 0.5 | 18 | 16 | 88.9 |
| 9 | Sap/CM(1h)->TNF[2] | 10, 0.5 | 20 | 2 | 10.0 |

[1]Treatment with saponin one hour prior to TNF injection.
[2]Treatment with saponin and collagen gel delivery matrix one hour prior to TNF injection.

The above results demonstrate that the toxicity of intralesionally administered TNF in conjunction with saponin can be reduced by introducing at least the saponin in a collagen gel delivery matrix. Although the toxicity of the therapy is reduced by employing a collagen gel delivery matrix, the efficacy of treatment does not concomitantly decrease. The results fuirther show that the efficacy of the TNF can be enhanced to a greater degree by administering the TNF simultaneously with the saponin/CM, though in a different vehicle.

EXAMPLE 2

Administration of Membrane Permeants Other Than Saponin with TNF

TABLE 4

Comparison of the Efficacy of Simultaneous vs. 1 Hour Preinjection of Saponin prior to TNF Injection With and Without Collagen Gel Delivery Matrix in RIF-1 Tumors in C3H Mice

| Grp | Treatment | Dose (mg/kg) | # of Tumors | Days to 4x Tumor Volume Treated | Days to 4x Tumor Volume Untreated | # of Deaths/ # of mice |
|---|---|---|---|---|---|---|
| 1 | Untreated Control | — | 8 | — | 8.2 ± 0.64 | 0/4 |
| 2 | Sap->TNF(simul)[1] | 10, 0.5 | 0 | — | — | 5/5 |
| 3 | Sap/CM->TNF(simul)[2] | 10, 0.5 | 5 | 20.0 ± 4.29 | — | 1/6 |
| 4 | Sap/CM/TNF[3] | 10, 0.5 | 6 | 16.8 ± 1.89 | — | 0/6 |
| 5 | Sap/CM(1h)->TNF[4] | 10, 0.5 | 4 | 15.3 ± 0.57 | — | 2/6 |
| 6 | Sap->TNF(simul)[1] | 10, 0.8 | 0 | — | — | 5/5 |
| 7 | Sap/CM->TNF(simul)[2] | 10, 0.8 | 3 | 21.7 ± 4.21 | — | 3/6 |
| 8 | Sap/CM/TNF[3] | 10, 0.8 | 5 | 15.2 ± 0.55 | — | 1/6 |
| 9 | Sap/CM(1h)->TNF[4] | 10, 0.8 | 2 | 14.6 ± 3.05 | — | 4/6 |

[1]Two simultaneous injections with two separate syringes, one containing saponin and the other containing TNF
[2]Two simultaneous injections with two separate syringes, one containing saponin and collagen gel delivery matrix and the other containing TNF
[3]One syringe containing a mixture of saponin, collagen gel delivery matrix and TNF
[4]Treatment with saponin and collagen gel delivery matrix one hour prior to TNF injection.

TABLE 5

Screening of Other Agents as Membrane Permeants to Enhance Intratumoral TNF Activity in RIF-1 Tumors in C3H Mice

| Grp | Treatment* | Permeant Dose (mg/kg) | TNF Dose (mg/kg) | # of Tumors | T/C[3] |
|---|---|---|---|---|---|
| 1 | TNF[1] | | 0.3 | 34 | 1.04 |
| 2 | Taurocholic Acid | 190 | — | 5 | 1.33 |
| 3 | Taur.(1 hr)–>TNF | 190 | 0.3 | 5 | 1.40 |
| 4 | Digitoxin | 40 | — | 5 | 0.99 |
| 5 | Digitoxin(1 hr)–>TNF | 40 | 0.3 | 5 | 1.40 |
| 6 | Lysolecithin(type 1) | 10 | — | 6 | 1.27 |
| 7 | Lyso.(1 hr)–>TNF | 10 | 0.3 | 6 | 1.46 |
| 8 | Lyso.(simul.)–>TNF[2] | 10 | 0.3 | 5 | 2.15 |

[1]Mean from 6 separate experiments
[2]Two simultaneous injections with two separate syringes, one containing lysolecithin (type 1) and the other containing TNF
[3]T/C: Ratio of tumor growth delay (days) of treated tumors to tumor growth delay of untreated controls.
*All membrane permeants were given intratumorally, one hour prior to TNF injection.

The above results demonstrate that other membrane permeant agents besides saponin, when administered either prior to or simultaneously with TNF, are capable of enhancing the efficacy of the intralesionally administered TNF.

EXAMPLE 3

Intralesional Administration of Agents other than TNF

TABLE 6

Screening of Other Therapeutic Agents for Enhancement of Efficacy by Saponin (10 mg/kg) in RIF-1 Tumors in C3H Mice

| Grp | Treatment[1] | Dose (mg/kg) | # of Tumors[2] | T/C[3] | Comments |
|---|---|---|---|---|---|
| 1 | Saponin | 10 | 13 | 1.2 | 2 deaths |
| 2 | Tyrphostin 47 | 60 | 5 | 1.1 | EtOH* |
| 3 | Saponin(1 hr)–>Tyr. 47 | 60 | 3 | 1.2 | EtOH*, 2 deaths |
| 4 | Brefeldin A(BFA) | 40 | 5 | 2.6 | DMSO* |
| 5 | Saponin(1 hr)–>BFA | 40 | 3 | 2.6 | DMSO*, 2 deaths |
| 6 | Decoyinine | 40 | 5 | 1.0 | |
| 7 | Saponin(1 hr)–>Decoy | 40 | 4 | 1.1 | |
| 8 | Genistein | 80 | 5 | 1.1 | |
| 9 | Saponin(1 hr)–> Genistein | 80 | 5 | 1.3 | |
| 10 | Neomycin sulfate (NS) | 40 | 8 | 0.7 | |
| 11 | Saponin (1h)–>NS | 40 | 8 | 1.1 | 1 death |
| 12 | AFC | 30 | 5 | 0.7 | |
| 13 | Saponin(1 hr)–>AFC | 30 | 4 | 1.1 | 1 death |
| 14 | Suramin | 20 | 5 | 1.0 | |
| 15 | Saponin (1 hr)–>Suramin | 20 | 1 | 1.8 | 5 deaths |
| 16 | Interferon-alpha (IFN-a) | 2 × 10[5]† | 6 | 0.8 | |
| 17 | Saponin(1 hr)–>(IFN-a) | 2 × 10[5]† | 5 | 1.1 | 1 death |

[1]Saponin administered as a free solution in saline one hour prior to injection of test active compound dissolved in saline, unless otherwise specified.
[2]Number of tumors reflects only surviving animals.
[3]T/C: Ratio of tumor growth delay (days) of treated tumors to tumor growth delay of untreated controls.
†values are in units/injection.
*As solvent

TABLE 7

Influence of Saponin With and Without Collagen Gel Delivery Matrix to Enhance the Efficacy of Vinblastine in RIF-1 Tumors in C3H Mice

| Grp | Treatment | Dose (mg/kg) | # of Tumors* | Treated | Toxicity Deaths/# mice |
|---|---|---|---|---|---|
| 1 | Untreated Control | — | 8 | 8.3 ± 0.49 | 0/4 |
| 2 | Saponin | 10 | 3 | 8.5 ± 0.32 | 2/5 |
| 3 | Saponin/CM | 10 | 5 | 8.1 ± 0.89 | 0/5 |
| 4 | Vinblastine(VLB) | 10, 4 | 5 | 14.1 ± 1.57 | 0/5 |
| 5 | Saponin(1 hr)–> VLB[1] | 10, 4 | 2 | 18.2 ± 0.31 | 3/5 |
| 6 | Sap/CM(1 hr)–> VLB[2] | 10, 4 | 5 | 14.1 ± 1.70 | 0/5 |
| 7 | Sap/CM/VLB[3] | 10, 4 | 5 | >24.1 ± 3.99[2] | 0/5 |

[1]Treatment with Saponin one hour prior to VLB injection.
[2]Treatment with Saponin and Collagen Matrix Delivery Gel one hour prior to VLB injection.
[3]One Syringe containing a mixture of Saponin, Collagen Matrix Delivery Gel and VLB
*Number of tumors reflects only surviving animals.

The above results demonstrate that intralesionally administering saponin can improve the efficacy of antiproliferative agents other than TNF. For example, the use of saponin in conjunction with vinblastine greatly enhances the efficacy of the vinblastine. Furthermore, use of a collagen gel matrix further enhances the efficacy of vinblastine while decreasing the observed lethal toxic side effects.

It is evident from the above results that improved methods of treating cellular proliferative diseases characterized by the presence of solid lesions through administration of chemotherapeutic agents, particularly chemotherapeutic agents that exhibit antiproliferative activity through intracellular activity, are provided. By using the subject method for intralesional administration, greater anti-cellular proliferative activity and/or reduced host toxicity is achieved.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An improved method for the site-specific administration of a chemotherapeutic agent across a cell memnbrane of diseased tissue in a host, the improvement comprising:
    introducing at the site of said diseased tissue a cell membrane permeant in a pharmaceutically acceptable vehicle capable of acting as a depot;
    wherein said cell membrane permeant is capable of disrupting the integrity of said cell membrane in said diseased tissue and improving the efficacy of a chemotherapeutic agent when said chemotherapeutic agent is used in conjunction with said cell membrane permeant.

2. The method according to claim 1, wherein said cell membrane permeant and said pharmaceutical agent are introduced simultaneously.

3. The method according to claim 1, wherein said cell membrane permeant and said pharmaceutical agent are introduced as a single composition.

4. The method according to claim 1, wherein said cell membrane permeant and said phamautical agent are introduced as two separate compositions.

5. The method according to claim 1, where said cell membrane permeant is selected from the group consisting of lysoplasmologens, ionic detergents, steroidal glycosides, triterpenoid glycosides, bile acids, digitalis and constitutents thereof; fusidic acid, melittin and polymyxin B.

6. A method for the site-specific administration of a chemotherapeutic agent across a cell membrane of diseased tissue in a host suffering from a cellular proliferative disease, said method comprising:

introducing at the site of a lesion of said cellular proliferative disease an intracellularly acting chemotherapeutic agent in conjunction with a cell membrane permeant in a pharmaceutically acceptable vehicle capable of acting as a depot, wherein said cell membrane permeant is capable of disrupting the integrity of a cell membrane when said composition is administered to said cell and said vehicle limits the systemic dispersion of said cell membrane permeant thereby reducing systemic toxicity;

whereby the rate of progression of said cellular proliferative disease is decreased.

7. The method according to claim 6, wherein said cell membrane permeant and said chemotherapeutic agent are introduced simultaneously.

8. The method according to claim 7, wherein said cell membrane permeant and said chemotherapeutic agent are introduced as a single composition in said pharmaceutically acceptable vehicle.

9. The method according to claim 6, wherein said cell membrane permeant is selected from the group consisting of lysoplasmologens, ionic detergents, triterpenoid glycosides, bile acids, fusidic acid, melittin and polymyxin B.

10. The method according to claim 6, wherein said intracellularly acting chemotherapeutic agent is a protein therapeutic.

11. The method according to claim 10, wherein said protein therapeutic is a naturally occurring cytotoxic factor.

12. The method according to claim 11, wherein said factor is selected from the group consisting of TNF-$\alpha$ and TNF-$\beta$.

13. The method according to claim 6, wherein said intracellularly acting chemotherapeutic agent is a vinca alkaloid.

14. The method according to claim 13, wherein said vinca alkaloid is vinblastine.

15. A method for the site-specific administration of a chemotherapeutic agent across a cell membrane of diseased tissue in a host suffering from a cellular proliferative disease, the method comprising:

introducing at the site of said diseased tissue a cell membrane permeant in a pharmaceutically acceptable vehicle capable of acting as a depot, wherein said pharmaceutically acceptable vehicle limits the systemic dispersion of said cell membrane permeant;

wherein said cell membrane permeant is capable of disrupting the integrity of said cell membrane in said diseased tissue and improving the efficacy of an intracellularly acting chemotherapeutic agent when said chemotherapeutic agent is used in conjunction with said cell membrane permeant.

16. The method according to claim 15, wherein said cell membrane permeant and said pharmaceutical agent are introduced simultaneously.

17. The method according to claim 15, wherein said cell membrane permeant and said pharmaceutical agent are introduced as a single composition.

18. The method according to claim 15, wherein said cell membrane permeant and said pharmaceutical agent are introduced as two separate compositions.

19. The method according to claim 15, where said cell membrane permeant is selected from the group consisting of lysoplasmologens, ionic detergents, triterpenoid glycosides, bile acids, fusidic acid, melittin and polymyxin B.

20. A composition suitable for intralesional administration across a cell membrane, consisting essentially of a cell membrane permeant in a pharmaceutically acceptable vehicle capable of acting as a depot, wherein said cell membrane permeant is capable of disrupting the integrity of said cell membrane when said composition is administered to said cell and said pharmaceutically acceptable vehicle limits the systemic dispersion of said cell membrane permeant thereby reducing the systemic toxicity of said composition.

21. The composition according to claim 20, wherein said cell membrane permeant comprises from 0.1 to 80 weight percent of said composition.

22. The composition according to claim 20, wherein said cell membrane permeant is selected from the group consisting of lysoplasmologens, ionic detergents, triterpenoid glycosides, bile acids, fusidic acid, melittin and polymyxin B.

23. The composition of claim 20, wherein said vehicle is proteinaceous.

24. The composition according to claim 20, further comprising an intracellularly acting chemotherapeutic agent.

25. The composition of claim 24, wherein said cell membrane permeant and said chemotherapeutic agent are both in said pharmaceutically acceptable vehicle.

26. A kit for treating a host suffering from a cellular proliferative disease through intralesional administration of a cell membrane permeant in conjunction with a chemotherapeutic agent, said kit comprising:

a cell membrane permeant; and
   a pharmaceutically acceptable vehicle capable of acting as a depot;

wherein said cell membrane permeant is capable of disrupting the integrity of a cell membrane when administered to said host and said pharmaceutically acceptable vehicle limits the systemic dispersion of said cell membrane permeant thereby reducing systemic toxicity.

27. The kit according to claim 26, wherein said cell membrane permeant is a saponin.

28. The kit according to claim 26, further comprising an effective amount of an intracellularly acting chemotherapeutic agent.

29. The kit according to claim 26, wherein said pharmaceutically acceptable vehicle is a proteinaceous matrix comprising collagen.

* * * * *